United States Patent [19]

Dabi

[11] Patent Number: 4,554,297
[45] Date of Patent: Nov. 19, 1985

[54] RESILIENT CELLULAR POLYMERS FROM AMINE TERMINATED POLY(OXYALKYLENE) AND POLYFUNCTIONAL EPOXIDES

[75] Inventor: Shmuel Dabi, Highland Park, N.J.

[73] Assignee: Personal Products Company, Milltown, N.J.

[21] Appl. No.: 485,782

[22] Filed: Apr. 18, 1983

[51] Int. Cl.$^4$ .................................................. C08J 9/08
[52] U.S. Cl. ..................... 521/178; 521/135; 525/523; 528/111
[58] Field of Search ................. 528/111; 521/178, 135

[56] References Cited

U.S. PATENT DOCUMENTS

| | | | |
|---|---|---|---|
| 3,306,809 | 2/1967 | Williamson et al. | 528/111 |
| 3,316,185 | 4/1967 | Reinking | 528/111 |
| 3,380,881 | 4/1968 | Williamson et al. | 528/361 |
| 3,462,393 | 8/1969 | Legler | 528/111 |
| 3,645,969 | 2/1972 | Harvey | 528/407 |
| 4,423,166 | 12/1983 | Moriority et al. | 528/111 |
| 4,423,170 | 12/1983 | Waddill | 528/111 |

FOREIGN PATENT DOCUMENTS 0030668  6/1981  European Pat. Off. ............ 521/178

OTHER PUBLICATIONS

Chem. Abstracts, vol. 95:116530p, 1981.

Primary Examiner—Morton Foelak
Attorney, Agent, or Firm—Jason Lipow

[57] ABSTRACT

An absorbent, flexible, resilient, cellular polymer is provided which comprises the reaction product of at least one epoxy resin and amine terminated poly(alkylene oxide).

18 Claims, No Drawings

RESILIENT CELLULAR POLYMERS FROM AMINE TERMINATED POLY(OXYALKYLENE) AND POLYFUNCTIONAL EPOXIDES

BACKGROUND OF THE INVENTION

This invention concerns providing resilient cellular polymers suitable for use in products for absorbing body fluids such as for example, sanitary napkins, catamenial tampons, diapers, bandages, surgical dressings and the like. Such materials, commonly referred to as foams, have already been considered for use in such products and various polymers and processes have been suggested as suitable. For example, newly developed polyurethane foams have been considered as well as polyester foams and cellulose foam.

While, in the main such prior suggested foams have been capable of absorbing body fluids to varying degrees, the properties of these prior materials have fallen short of those preferred for products such as are considered herein. Ideally, for a product such as a diaper, a sanitary napkin or catamenial tampon, a foam material should provide substantial capacity for absorbing body fluids. The foam should be resilient and soft so as to provide user comfort and conform to the body as the user exerts stress on the product when worn. The foam should be able to efficiently carry fluid deposited on its surface into the body of the foam, i.e., the foam should exhibit efficient wicking. Needless to say, the foam should consist solely of biologically acceptable material.

Prior suggested foams have, in one respect or another, fallen short of these ideal properties. For example, cellulose and polyvinyl alcohol foams are stiff and uncomfortable. Polyurethane and polyvinyl chloride foams are soft and resilient and may be modified to be absorbent to a degree, but inherently lack the property of efficient wicking. Accordingly, there is a need for a cellular polymeric material, i.e., a foam, which more closely approaches ideal properties.

SUMMARY OF THE INVENTION

In accordance with the teachings of this invention a cellular polymeric material is provided which combines the desired properties of absorbency, softness, resiliency, efficient wicking and biological compatability to a degree not found in any prior material. Specifically, it has been discovered that such an absorbent, flexible, resilient cellular foam may be provided which comprises the reaction product of at least one epoxy resin and amine terminated poly(alkylene oxide). The amine terminated polymer may be selected from the group consisting of amine terminated poly(propylene oxide), amine terminated poly(ethylene oxide), amine terminated copolymers of ethylene oxide and propylene oxide, and mixtures thereof. The selections must be such that, in the aggregate, the ratio of ethylene oxide groups to propylene oxide groups in the reaction mixture is from about 1.0 to about 15.0 and, preferably, from about 3.0 to about 10.0. For convenience, it is preferred that copolymers of the alkylene oxides are employed.

A wide variety of epoxy monomers and polymers are suitable for use and are well known in the art. It is preferred that the epoxy resin be supplied to the reaction mix such that in the aggregate, the reaction mixture comprises from about 1.0 to about 3.0 epoxy groups per amine group and still more preferably from about 1.2 to about 1.8 epoxy groups per amine group. The epoxy resin of choice are the di- and polyglycidyl ethers of bisphenols, the bisphenols having the formula

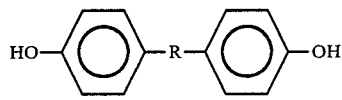

wherein R is a bivalent radical containing 1 to 8 atoms of C, O, S, and/or N and more preferably, an alkylene or alkylidene groups containing 1 to 8 carbon atoms or still more preferably 1 to 6 carbon atoms.

The foam is prepared by combining the reactants at room temperature or more preferably at an elevated temperature to form an intermediate reaction product which is preferably at the point in the reaction just prior to gelation. A blowing agent then is introduced to create the cells of the foam. A preferable blowing agent is one which releases $CO_2$ gas upon activation and, when this is used in combination with the teachings of this invention, the resulting foam advantageously exhibits a snow-white appearance.

DETAILED DESCRIPTION OF THE INVENTION

The invention provides a foam which is the reaction product of amine terminated poly(alkylene oxide) and epoxy resin.

The amine terminated poly(alkylene oxide) may be in the form of mixtures of amine terminated poly(alkylene oxides), copolymers of alkylene oxides such as random copolymers or block copolymers, or even mixtures of the above. It is important however, that such reaction mixture be provided with a sufficiently high enough ratio of ethylene oxide groups to propylene oxide groups so that the resulting reaction product has the desired degree of hydrophilicity. On the other hand, this ratio of ethylene oxide to propylene oxide group must be low enough to produce a reaction product with the desired resiliency. A preferred range for this ratio which produces a suitably hydrophilic, resilient foam is from about 1 to about 15 ethylene oxide groups per propylene oxide group and still more preferably from about 3 ethylene oxide groups to about 10 ethylene oxide groups per propylene oxide group.

Amine terminated poly(alkylene oxides) are commercially available, one such source being the series of polymers sold by the Texaco Chemical Company of Bellaire Texas, under the trademark "Jeffamine" compounds. A particularly useful series of Jeffamine compounds are designated by Texaco as Jeffamine ED compounds and have the structure:

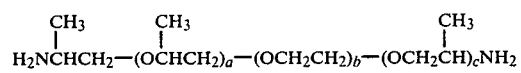

These block copolymers are derived from propylene oxide-capped polyethylene glycol and are available from Texaco as compounds wherein the a, b, and c values are in the following ratios:

| Jeffamine Compound | Approximate Value of | |
|---|---|---|
| | b | a + c |
| ED-600 | 13.5 | 3.5 |
| ED-900 | 20.5 | 3.5 |

-continued

| Jeffamine Compound | Approximate Value of | |
|---|---|---|
| | b | a + c |
| ED 2001 | 45.5 | 3.5 |

Suitable foams have also been prepared by combining these amine terminated poly(alkylene oxides) with a polyoxypropylene amine sold by the Texaco Chemical Company under the name JEFFAMINE T-403 and having the following chemical structure:

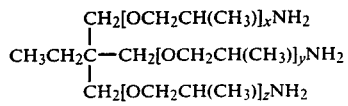

wherein the sum of x+y+z is equal to about 8.3.

Many epoxy monomer and polymer are suitable for use. Such epoxy resins have already been suggested for use in providing hydrophobic foams from amine-terminated liquid polymers and are described in a European Patent Application, number 80107479.0, of the B. F. Goodrich Company claiming priority to a United States application filed on December 3, 1979 and published June 24, 1981. The epoxy resins described therein and usable in producing the resilient, absorbent, hydrophilic foams of this invention contain at least an average of about 1.7 epoxy groups per molecule, more preferably from about 1.7 to about 4 epoxy groups per molecule, and even more preferably from about 1.7 to about 2.3 epoxy groups per molecule. The epoxy resins may be liquids or low-melting solids but are preferably liquids having a bulk viscosity from about 200 centipoises to about 2,000,000 centipoises, measured using a Brookfield RVT viscometer at 25° C. The epoxy resins can have an epoxy equivalent weight, i.e., gram molecular weight per epoxy group, from about 70 to about 6,000, more preferably from about 70 to about 2,000. Examples of suitable polyglycidyl esters of polycarboxylic acids include the diglycidyl ester of linoleic dimer acid, the triglycidyl ester of linoleic trimer acid, and the like. Suitable glycidyl ether resins include polyallyl glycidyl ether, and diglycidyl ether of chlorendic diol, the diglycidyl ether of dioxanediol, the diglycidyl ether of endomethylene cyclohexanediol, epoxy novolac resins, alkanediol diglycidyl ethers, alkanetriol triglycidyl ethers, and the like. More preferred glycidyl ether resins include alkanediol diglycidyl ethers having the formula

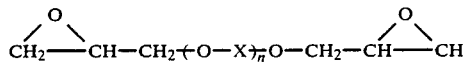

wherein X is an alkylene or alkylidene group containing from 1 to 10 carbon atoms, more preferably from 2 to 6 carbon atoms, and n is from 1 to 25, more preferably from 1 to 15. Suitable alkanediol diglycidyl ethers include ethylene glycol diglycidyl ether, propylene glycol diglycidyl ether, butanediol diglycidyl ether, and the like. Other more preferred glycidyl ether resins include alkanetriol triglycidyl ethers wherein the alkane group contains from 2 to 10 carbon atoms, more preferably from 3 to 6 carbon atoms, such as glyceryl triglycidyl ether, the triglycidyl ether of trimethylolpropane, and the like.

This class of glycidyl ether resins produces a foam, in accordance with the teachings of this invention, which is soft, absorbent and resilient. Unfortunately, this group reacts disadvantageously slowly. A most preferred class of glycidyl ether resins is the di- and polyglycidyl ethers of bisphenols, the bisphenols having the formula

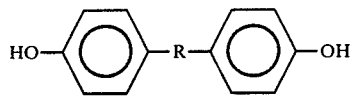

wherein R is a bivalent radical containing 1 to 8 atoms of C, O, S and/or N, more preferably an alkylene or alkylidene groups containing 1 to 8 carbon atoms, and even more preferably an alkylene or alkylidene groups containing 1 to 6 carbon atoms. Examples of suitable bisphenols include methylene bisphenol, isopropylidene bisphenol, butylidene bisphenol, octylidene bisphenol, bisphenol sulfide, bisphenol ether, bisphenol amine, and the like. Excellent results were obtained using isopropylidene bisphenol. The latter epoxy resin not only produces a foam with the desired properties but also is quite reactive and is most suitable for use in connection with the teachings of this invention.

The proportions of epoxy resin to amine terminated poly(alkylene oxide) in the reaction mixture may vary over a substantial range. Preferably, the ratio of active epoxy groups to amine groups may range from about 1 to about 3. More preferably this ratio varies from about 1.2 to about 1.8 epoxy groups per amine group.

The production of the foams of this invention is best carried out using a two step process consisting of first performing an intermediate reaction step and then foaming the reaction mixture as polymerization continues.

The intermediate reaction step is carried out by first mixing the epoxy resin and amine terminated poly(alkylene oxide) in the proportions taught herein. The reaction mixture is then heated and maintained at a reaction temperature which may range from about 25° C. to about 130° C. In practise, temperatures much below 50° C. will require a disadvantageously long reaction time whereas temperatures above 110° C. will result in a reaction time which is too short and hence difficult to control. Accordingly, a preferable temperature range is between about 50° C. and about 110° C. with a range of about 65° C. to about 110° C. being most preferable. As the reaction proceeds and polymerization occurs between the epoxy resin and amine terminated (alkylene oxide), the viscosity of the reaction mixture rises. The degree of intermediate reaction may be monitored and controlled by a continuous or incremental measurement of the reaction mixture viscosity. Alternatively, other properties could be measured which indicate the progress of the reaction e.g., density, refractive index, mechanical or electrical properties or the like.

Irrespective of what properties are ued to measure the progress of the reaction, as the reaction proceeds, the mixture passes from the liquid state to that of a relatively inelastic solid. The transition state between liquid and solid is generally referred to as the gelation state and, ideally, it is just prior to this point in the reaction process that a blowing agent should be introduced to produce a stable foam having uniform cells. Too early an introduction of blowing agent results in the gas diffusing through the relatively liquid reaction mixture and hence failing to form stable cells. Too late an introduction will result in the now substantially solidified reaction mixture being too inelastic to allow the gas to form cells.

It has been discovered that advantageously a foaming agent introduced when the reaction mixture reaches a viscosity of from about 1000 cps. to about 12,000 cps (measured at 25° C.). Depending primarily on the temperature at which the reaction is run, typically such viscosity range can be reached in a time period of as short as 10 minutes or as long as two hours.

A wide variety of foaming agents may be employed. For example, certain compounds may be introduced which release gases upon heating. Examples of this type of foaming agent are azo bis(isobutyronitril) and benzene sulfonyl hydrazide which release nitrogen gas when heated.

A preferred method of foaming is to mix into the reaction mixture a compound or mixture of compounds such as sodium carbonate or sodium bicarbonate. Upon the addition of a suitable acid or acidic salt, these compounds react to release carbon dioxide gas to perform the foaming. Suitable acids or acid compounds may be for example, hydrochloric acid; phosphoric acid; organic acids such as acetic, lactic, citric, etc., sodium bisulfite; potassium dihydrogen phosphate or the like.

The foaming agents may be added to the initial copolymerization reaction mixture when such mixture is at a temperature of from 30° C. to about 110° C. Preferably, to have a controlled release of carbon dioxide, for example, the reaction mixture should be at a temperature ranging from about 40° C. to about 80° C. Accordingly, it may be necessary to first reduce the temperature of the initial copolymerization reaction mix prior to adding the foaming agents. After foaming is initiated, the foaming is completed by heating, preferably in an oven for about five to about twenty minutes at an elevated temperature ranging from about 120° C. to about 140° C.

EXAMPLES 1-6

A series of foams are prepared by reacting various combinations of Jeffamine amine terminated poly(alkylene oxide) polymers with epoxy resins in an intermediate reaction step, cooling the reaction mixture, in some cases, and then combining the reaction mixture with blowing agents by mixing the blowing agents into the reaction mixture for about 30 seconds. The reaction mixture is then foamed and cured by heating in an oven at vaious temperatures over various time intervals. Table 1 below sets out the starting reactants (in parts by weight) and conditions under which these reactants were combined in the initial copolymerization step:

TABLE 1

| | Jeffamine Polymer | | | | Epoxy Resin | | Intermediate Reaction Conditions | | | |
|---|---|---|---|---|---|---|---|---|---|---|
| Sample | T-403 | ED-600 | ED-900 | ED-2001 | EPON 828* | A508** | Reaction Temp (°C.) | Reaction Time (Min) | Cooling Temp (°C.) | Cooling Time (Min) |
| 1 | 7.7 | 42.0 | — | — | 39.3 | — | 95 | 15 | 95 | — |
| 2 | 12.8 | 8.3 | — | 27.7 | 41.6 | — | 110 | 15 | 80 | 10 |
| 3 | 12.3 | — | — | 40.4 | 35.2 | — | 125 | — | 70 | 30 |
| 4 | 2.8 | — | 36.6 | — | 33.8 | — | 130 | 10 | 70 | 10 |
| 5 | 4.7 | 18.4 | — | — | 17.3 | 38.6 | 135 | 10 | 100 | 10 |
| 6 | — | 20.0 | 31.1 | — | 44.4 | — | 110 | 10 | 70 | 15 |

*EPON 828 is a diglycidylether of bisphenol A sold under the tradename EPON 828 by the Shell Oil Co.
**A-508 is diglycidylether of bisphenol A diluted with an epoxidized polyol and sold under this tradename by Ciba-Geigy, Inc.

Table 2 below sets out the foaming agents in parts per weight and the foaming and curing conditions:

TABLE 2

| | Foaming and Curing | | | | | |
|---|---|---|---|---|---|---|
| | Foaming Agent | | | Foam and Cure Conditions | | |
| Sample | 50% By Weight NaHCO$_3$ in Water | 50% Aqueous H$_3$PO$_4$ | ABIN* | Mixing Temp (°C.) | Curing Temp (°C.) | Curing Temp (Min) |
| 1 | 4.0 | 7.0 | — | 95 | 125 | 10 |
| 2 | 4.0 | 5.6 | — | 80 | 120 | 15 |
| 3 | 5.7 | 6.4 | — | 70 | 125 | 20 |
| 4 | 11.2 | 15.6 | — | 70 | 135 | 15 |
| 5 | 15.3 | 5.7 | — | 60 | 135 | 30 |
| 6 | — | — | 4.5 | 70 | 130 | 10 |

*ABIN is azo bis (isobutyronitril)

Samples 1-6 are tested to determine their various properties. Absorbency, expressed as weight of water absorbed per unit weight of dry foam is determined by weighing a sample of the foam dry and then totally immersing the foam sample in a container of water. The sample is removed from the container and weighed without the application of external pressure. The results are reported below in units of grams of water per gram of dry foam.

Resiliency is tested by applying pressure to compress a sample of the foam to 50% of its original height and maintaining the foam in the compressed state for one minute. The pressure is then released and the foam is allowed to recover. The percent recovery, based on the original height of the uncompressed foam, after one minute of recovery is reported in Table 3 below.

The density of the foam is determined by measuring the dimension of a sample of foam, weighing the sample and reporting the density in Table 3 below as the weight, in grams, per unit volume, in cubic centimeters.

Vertical wicking is determined by immersing the tip of a foam strip measuring ¼ inch by ¼ inch by 2 inches long, into a beaker of water while the strip is held vertically (i.e., the longitudinal direction is vertical) above the beaker. The time required for the water to climb 1.5 inches is recorded in Table 3 below.

TABLE 3

| Sample | Absorption gm./gm. | Properties of Foam Resiliency % Recovery | Vertical Wicking secs. | Density gm./cm³ |
|---|---|---|---|---|
| 1 | 10 | 99.5 | 76 sec. | 0.14 |
| 2 | — | — | — | — |
| 3 | 8 | 92.0 | 60 sec. | 0.22 |
| 4 | 12 | 99.5 | — | 0.67 |
| 5 | 8 | 100.0 | 100 sec. | 0.2 |
| 6 | 15 | 98.0 | — | 0.08 |

EXAMPLES 7-14

A series of samples are produced by using the procedure of examples 1-6 with the exception that no foaming agents are introduced, thereby resulting in reaction products in the form of films. This is done to illustrate the effects of varying the ratio of epoxy groups to amine groups (E/A) in the initial reaction mix as well as the ratio of ethylene oxide groups to propylene oxide groups (EO/PO) in the amine terminated poly(alkylene oxide) polymer. The foaming step is eliminated to avoid the variables of foam cell structure and density in illustrating how the properties vary with varying EO/PO and E/A ratios. The properties reported below in Table 4 are Young's Modulus and the Glass Transition temperature which relate to rigidity and elasticity of the reaction products. Water aborption is likewise recorded and is measured by weighing a sample of the film, and then immersing the film in water for fourteen days. The weight of water absorbed expressed as a percentage of the dry weight of the film, is reported in Table 4 below.

TABLE 4

| Sample | E/A | EO/PO | Young's Mod. (PSI) | Glass Trans. Temp. (°C.) | Water Absorption % |
|---|---|---|---|---|---|
| 7 | 1.00 | 3.85 | 160 | −17 | 58 |
| 8 | 1.00 | 5.85 | 126 | −35 | 115 |
| 9 | 1.17 | 3.85 | 337 | −12 | 41 |
| 10 | 1.17 | 5.85 | 293 | −35 | 85 |
| 11 | 1.66 | 3.85 | 600 | +4 | 23 |
| 12 | 1.66 | 5.85 | 485 | −22 | 75 |
| 13 | 2.03 | 3.85 | 796 | +21 | 7.7 |
| 14 | 2.03 | 5.85 | 664 | −15 | 28.8 |

Referring now to Table 4 and specifically to samples 7, 9, 11, and 13, it can be seen that at a constant EO/PO ratio of 3.85, as the E/A ratio increases from 1.00 to 2.03, the Young's Modulus increases from 160 to 796 and the glass transition temperature increases from −17° C. to +21° C. This indicates an increasing rigidity and inelasticity with increasing E/A ratio.

Further, it can be seen that as the E/A ratio increases through the range of 1.0 to 2.03, the water absorbency decreases from 58% to 7.7%.

Similarly, when referring to samples 8, 10, 12, and 14, at a second constant value of EO/PO ratio of 5.85, the above described relationships pertain.

The above data is consistent with the discovery that the E/A ratio must be carefully balanced to produce a foamed polymer suitable for use in accordance with the teachings of this invention. At high E/A ratios the polymer is too rigid and inelastic, and concomitantly the resulting foam will be inflexible. Further, the foam will be relatively non-absorbent. At low E/A ratios the polymer is weak, extremely elastic and in some instances disadvantageously tacky. Accordingly, cell walls will collapse during foaming and curing. By operating within the range of E/A ratios prescribed herein suitable foams may be provided.

Again referring to Table 4, reference is made to the set of paired samples 7 and 8, 9 and 10, 11 and 12, 13 and 14. Each pair illustrates two samples at a constant E/A ratio, with one sample at a low EO/PO ratio and a second sample at a high EO/PO ratio. It shall be noted that as the EO/PO ratio is increased the sample becomes less rigid, more elastic and more absorbent. Again, by operating within the teachings set out herein with respect to EO/PO ratio a suitable foam may be obtained.

What is claimed is:

1. A product for absorbing body fluids comprising as an absorbent element therein, a cellular hydrophilic polymeric material, said polymeric material comprising the reaction product of at least one epoxy resin and amine terminated poly(alkylene oxide) selected from the group consisting of amine terminated poly(propylene oxide), amine terminated poly(ethylene oxide), amine terminated copolymers of ethylene oxide and propylene oxide, and mixtures thereof wherein the ratio of ethylene oxide groups to propylene oxide groups in the reaction mixture ranges from about 1 to about 15.

2. The product of claim 1 wherein the ratio of ethylene oxide group to propylene oxide groups in the reaction mixture ranges from about 3 to about 10.

3. The product of claim 1 wherein the reaction mixture comprises from about 1 to about 3 epoxy groups per amine group.

4. The product of claim 3 wherein the reaction mixture comprises from about 1.2 to about 1.8 epoxy groups per amine group.

5. The product of claim 1 wherein said amine terminated poly(alkylene oxide) comprises a compound having the empirical formula:

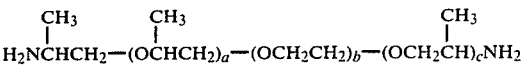

wherein b has an empirical value of from about 10 to about 50 and the sum of a and c has an empirical value of from about 1 to about 5.

6. The product of claim 1 wherein said amine terminated poly(alkylene oxide) comprises a compound having the empirical formula:

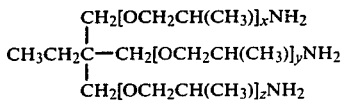

wherein the sum of x+y+z is equal to about 7 to about 10.

7. The product of claim 1 wherein said epoxy resin has an average ratio of epoxy groups per molecule of epoxy resin of at least 1.7.

8. The product of claim 7 wherein said epoxy resin has an average ratio of epoxy group per molecule of epoxy resin ranging from about 1.7 to about 4.

9. The product of claim 1 wherein said epoxy resin comprises a polyglycidyl ester of a polycarboxylic acid.

10. The product of claim 1 wherein said epoxy resin comprises a glycidyl ether resin.

11. The product of claim 10 wherein said epoxy resin comprises an alkanediol diglycidyl ether having the formula:

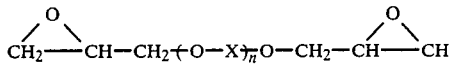

wherein x is selected from the group comprising alkylene or alkylidene group containing from 1 to 10 carbon atoms, and n has a value of from 1 to 25.

12. The product of claim 10 wherein said epoxy resin is selected from the group consisting of di- and polyglycidyl ethers of bisphenols, said bisphenols having the formula:

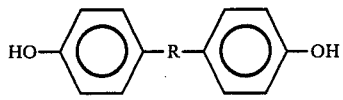

wherein R is a bivalent radical containing 1 to 8 atoms selected from the group consisting of C, O, S, or N.

13. The product of claim 12 wherein R is selected from the group consisting of alkylene or alkylidene radicals containing from about 1 to about 8 carbon atoms.

14. The product of claim 13 wherein said epoxy resin comprises isoproplidene bisphenol.

15. The product of claim 1 wherein said product is a sanitary napkin.

16. The product of claim 1 wherein said product is a catamenial tampon.

17. The product of claim 1 wherein said product is a disposable diaper.

18. The product of claim 1 wherein said product is a wound dressing.

* * * * *